United States Patent [19]
Ichikawa et al.

[11] 4,110,403
[45] Aug. 29, 1978

[54] PROCESS FOR PREPARING β,γ-UNSATURATED ALDEHYDES

[75] Inventors: Yataro Ichikawa; Osamu Kobayashi, both of Iwakuni; Kazuhiko Soma, Kawasaki; Tatuyuki Naruchi, Iwakuni; Yoshiyuki Yamanaka, Iwakuni; Nobuo Suzuki, Iwakuni, all of Japan

[73] Assignee: Teijin Limited, Osaka, Japan

[21] Appl. No.: 569,686

[22] Filed: Apr. 21, 1975

[30] Foreign Application Priority Data

Apr. 22, 1974 [JP] Japan .................................. 49-44402
Apr. 22, 1974 [JP] Japan .................................. 49-44403
Sep. 30, 1974 [JP] Japan .................................. 49-111643

[51] Int. Cl.$^2$ ............................................. C07C 45/00
[52] U.S. Cl. .................................. 260/603 R; 260/598; 260/599; 568/700; 568/813; 568/828; 568/879
[58] Field of Search ............... 260/603 R, 638 R, 599, 260/598, 618 R, 617 R

[56] References Cited

U.S. PATENT DOCUMENTS

| 2,042,220 | 5/1936 | Groll et al. ...................... 260/603 R |
| 2,308,192 | 1/1943 | Mikesko et al. ............. 260/638 R X |
| 2,335,027 | 11/1943 | Ritter ............................... 260/638 R |

*Primary Examiner*—Bernard Helfin
*Attorney, Agent, or Firm*—Sherman & Shalloway

[57] ABSTRACT

A process for preparing β,γ-unsaturated aldehydes which comprises dehydrogenating β,γ-unsaturated alcohols in the vapor phase, preferably in the substantial absence of oxygen, using copper having a specific surface area of 0.01 to 1.5 m$^2$/g as a catalyst at a temperature of 150° to 300° C. The β,γ-unsaturated aldehydes can be recovered in pure form by distilling the dehydrogenation reaction mixture in the presence of water. The starting β,γ-unsaturated alcohols can be prepared by reacting olefins with formaldehyde or a derivative capable of forming formaldehyde at a temperature of 180° to 400° C. in the absence of a solvent or in the presence of a non-aqueous organic solvent after pre-heating said formaldehyde or derivative to a temperature of 85° to 150° C.

19 Claims, No Drawings

PROCESS FOR PREPARING β,γ-UNSATURATED ALDEHYDES

This invention relates to a process for preparing β, γ-unsaturated aldehydes from β, γ-unsaturated alcohols. The invention also provides an improved process for preparing the β, γ-unsaturated alcohols, and also a novel process for purifying the β, γ-unsaturated aldehydes.

More specifically, this invention relates to a process for preparing β, γ-unsaturated aldehydes of formula (II) by dehydrogenating β, γ-unsaturated alcohols of formula (I), as shown by the following reaction scheme.

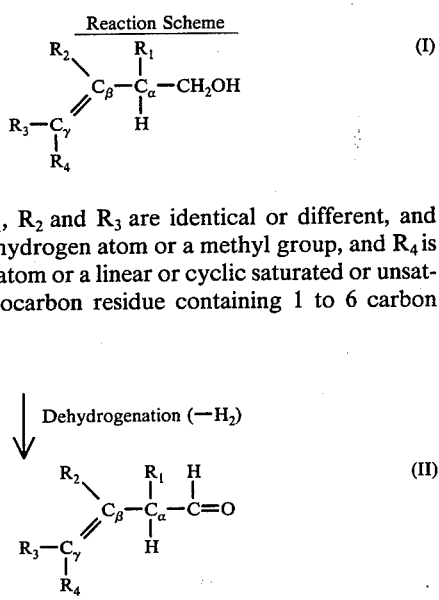

(wherein $R_1$, $R_2$ and $R_3$ are identical or different, and represent a hydrogen atom or a methyl group, and $R_4$ is a hydrogen atom or a linear or cyclic saturated or unsaturated hydrocarbon residue containing 1 to 6 carbon atoms)

(wherein $R_1$, $R_2$, $R_3$ and $R_4$ are the same as defined in formula (I))

Processes have previously been known to prepare saturated aldehydes at high selectivities by dehydrogenating corresponding saturated alcohols. Methods have also been known to prepare α, β-unsaturated aldehydes by dehydrogenating α, β-unsaturated alcohols. In the dehydrogenation of α,β-unsaturated alcohols, however, saturated aldehydes are formed as by-products, and the selectivity of the α,β-unsaturated aldehydes is low.

When β,γ-unsaturated alcohols are dehydrogenated by conventional processes, not only are saturated aldehydes formed as by-products, but there is also a marked formation of α,β-unsaturated aldehydes, and it is extremely difficult to obtain β,γ-unsaturated aldehydes.

To the best of our knowledge, U.S. Pat. No. 2,042,220 is believed to be the only report which describes the dehydrogenation reaction of β,γ-unsaturated alcohols. Example 2 of this U.S. Pat. No. states that 2-methyl-1-buten-4-al of the formula

is prepared by contacting 2-methyl-1-buten-4-ol of the formula

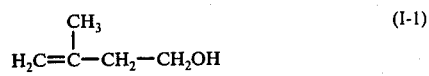

with a copper catalyst together with air. However, the product of formula (II-1) in Example 2 of the above U.S. Pat. No. was misidentified, and Chemical Communication 1395 (1970) later pointed out that the product obtained in Example 2 of the above U.S. Pat. No. was in fact 2-methyl-2-buten-4-al of the formula

which is a kind of α,β-unsaturated aldehyde.

On the other hand, German OLS No. 2,020,865 discloses a process for preparing α,β-unsaturated aldehydes in high yield by contacting β,γ-unsaturated aldehydes with a mixed catalyst comprising zinc oxide, metallic copper, silver and/or zinc, and a metallic oxide of an element of a sub-group, but does not at all teach the formation of β,γ-unsaturated aldehydes.

Accordingly, it is an object of this invention to provide a process for preparing β,γ-unsaturated aldehydes of formula (II) in high selectivities and yield from β,γ-unsaturated alcohols of formula (I).

Another object of this invention is to provide a process for preparing β,γ-unsaturated aldehydes of formula (II) in high selectivities from the β, γ-unsaturated alcohols while inhibiting the formation of by-product saturated aldehydes and α,β-unsaturated aldehydes.

Still another object of this invention is to provide a process for recovering purified β,γ-unsaturated aldehydes by separating saturated aldehydes from the curde β,γ-unsaturated aldehydes prepared by the process of this invention.

A further object of this invention is to provide a process for preparing β,γ-unsaturated alcohols to be used as a raw material in the process of this invention mentioned above.

Other objects and advantages of this invention will become apparent from the following description.

According to this invention, β,γ-unsaturated aldehydes of the formula

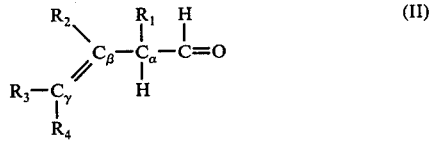

wherein $R_1$, $R_2$, $R_3$ and $R_4$ are the same as defined in formula (I), can be prepared in high selectivities by contacting β,γ-unsaturated alcohols of the formula

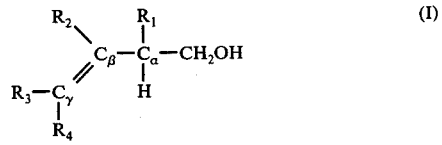

wherein $R_1$, $R_2$ and $R_3$ are identical or different, and represent a hydrogen atom or a methyl group, and $R_4$ is a hydrogen atom or a linear or cyclic saturated or unsaturated hydrocarbon residue containing 1 to 6 carbon atoms, in the vapor phase with copper having a specific surface area of 0.01 to 1.5 m$^2$/g as a catalyst at a temperature of 150° to 300° C.

In the above process of this invention, the concentration of oxygen in the reaction system must be adjusted to not more than 1/10 molar time the $\beta,\gamma$-unsaturated alcohol, and is preferably as low as possible. It is especially advantageous therefore to perform the above reaction in the substantial absence of oxygen. According to the work of the inventors of the present application, the formation of an $\alpha,\beta$-unsaturated aldehyde of formula (B-1) as a main product in Example 2 of U.S. Pat. No. 2,042,220 is probably due to the fact that in the reaction of the U.S. Pat., a stoichiometrical amount (equimolar amount), based on the starting $\beta,\gamma$-unsaturated alcohol of formula (I-1), of oxygen was caused to participate.

Examples of the $\beta,\gamma$-unsaturated alcohols of formula (I) used as a raw material in the above process include 1-buten-4-ol, 2-methyl-1-buten-4-ol, 2,3-dimethyl-1-buten-4-ol, 3-methyl-1-buten-4-ol, 2-penten-5-ol, 2-methyl-2-penten-5-ol, 3-methyl-2-penten5-ol, 3-hexen-6-ol, 3-methyl-3-hexen-6-ol, 4-methyl-3-hexen-6-ol, 4-methyl-3-hexen-6-ol, 4-methyl-1,3-hexadien-6-ol, 5-methyl-4-hepten-7-ol, 2,4-diemthyl-3-hexen7-ol, 2,4-diemthyl-1,3-hexadien-7-ol, 6-methyl-5-octene-8-ol, 2,5-dimethyl-4-hepten-7-ol, 2,5-diemthyl-2,4-heptdien-7-ol, 2,6-diemthyl-2,4-heptadien-7-ol, 2,6-dimethyl-5-octen-8-ol, 2,6-diemthyl-2,5-octadien-8-ol, 1-cyclohexyl-1-buten-4-ol, 1-cyclohexyl-2-methyl-1-buten-4-ol, 1-phenyl-1-buten-4-ol, and 1-phenyl-2-methyl-1-buten-4-ol. In the general formula (I), R$_4$ is preferably a hydrogen atom or an alkyl group containing 1 to 3 carbon atoms. Especially, 2-methyl-1-buten-4-ol corresponding to the formula (I) in which R$_1$ is a hydrogen atom, R$_2$ a methyl group, and R$_3$ and R$_4$ are each hydrogen atoms are preferred, and this compound can be prepared by reacting isobutene and formaldehyde at an elevated temperature.

The catalyst used in the process of this invention is metallic copper having a specific surface area of 0.01 to 1.5 m$^2$/g. Specific surface areas of less than 0.01 m$^2$/g are not preferred because the catalyst has too low an activity. If the specific surface area of the copper catalyst is above 1.5 m$^2$/g, the amount of by-product $\beta,\gamma$-unsaturated aldehyde becomes larger, and the amount of by-product saturated aldehyde also increases.

The copper catalyst used in this invention can be prepared by various methods such as a method comprising air-oxidizing a powdery, linear or net-like metallic copper at a high temperature to form copper oxide, and if desired, molding and then reducing it, a method comprising calcining a copper compound convertible to copper oxide by heat decomposition, such as copper hydroxide, basic copper carbonate or copper nitrate, under suitable conditions, and if desired, molding and then reducing it or a method comprising preparing copper or a copper compound supported on an inert carrier such as silicon carbide or diatomeceous earth in the same way as in the abovecited methods.

When the catalyst is prepared by air-oxidizing a powdery, linear or net-like metallic copper, oxidizing the copper to its inside causes the catalyst to have a high activity and a long active lifetime. In this case, higher temperatures and longer periods of reaction are required with larger diameters of the powdery, linear or net-like metallic copper.

When the reaction is carried out for long periods of time by the process of this invention, the activity of the copper catalyst is reduced. However, the catalyst can be easily activated by a customary manner, for example, by oxidizing the copper catalyst with molecular oxygen and then reducing it with a reducing agent such as hydrogen.

The dehydrogenation reaction in accordance with this invention is carried out at a temperature of 150° to 300° C., preferably 180° to 280° C., more preferably 220° to 270° C. If the temperature is lower than 150° C., the yield of a $\beta,\gamma$-unsaturated aldehyde per unit amount of the catalyst decreases. On the other hand, when the temperature exceeds 300° C., the active lifetime of the catalyst becomes shorter, and side reactions occur prominently.

The suitable WHSV (the weight of the $\beta,\gamma$-unsaturated alcohol in the raw material fed per unit weight of the catalyst per hour) is 0.01 to 1.0 g/g.hr although it differs according to the structure and molecular weight of the $\beta,\gamma$-unsaturated alcohol, the form of the catalyst, the activity of the catalyst based on its specific surface area, its form or the purity of copper, the concentration (partial pressure) of the $\beta,\gamma$-unsaturated alcohol, the reaction pressure, etc.

Furthermore, according to this invention, the active lifetime of the catalyst can be prolonged remarkably and its activity can be maintained for long periods of time by contacting the catalyst in the vapor phase with the $\beta,\gamma$-unsaturated alcohol of formula (I) in the presence of steam in the above-mentioned process of this invention. Thus, by performing the process of this invention in the presence of steam, the reaction can be continued while maintaining the desirable conversion of the $\beta,\gamma$-unsaturated aldehyde for a long period of time. This results in an increase in the total selectivity of the $\beta,\gamma$-unsaturated aldehyde of formula (II) and its yield.

When steam is used, the $\beta,\gamma$-unsaturated alcohol and the steam should be contacted simultaneously with the copper catalyst in the vapor phase at the temperatures described above.

The preferred amount of steam is 2 to 50 mols, desirably 5 to 20 mols, per mol of the $\beta,\gamma$-unsaturated alcohol. If the amount of steam is below the lower limit of the abovespecified range, the effect obtainable by using steam is reduced, and when the amount exceeds the upper limit, the yield of the $\beta,\gamma$-unsaturated aldehyde per unit weight of the catalyst per unit time is reduced.

The process of this invention is carried out by contacting the $\beta,\gamma$-unsaturated alcohol, with or without steam, in the vapor phase with the catalyst maintained at the reaction temperature described above. The partial pressure of the $\beta,\gamma$-unsaturated alcohol in this process is 0.01 to 0.2 atm., preferably 0.02 to 0.15 atm. If the partial pressure of the $\beta,\gamma$-unsaturated alcohol exceeds 0.2 atm., the amount of by-products such as a saturated aldehyde increases remarkably. When the partial pressure is lower than 0.01 atm., it brings about the disadvantage that a high degree of vacuum is required or a large amount of a carrier gas is needed.

The reaction pressure used in the process of this invention may be normal atmospheric pressure or an elevated or reduced pressure, and can be obtained by adjusting the partial pressure of the starting $\beta,\gamma$-unsaturated alcohol to the suitable range mentioned above using steam or another carrier gas.

The carrier gas may be any gas which does not adversely affect the $\beta,\gamma$-unsaturated alcohol and the reaction itself. Examples of the carrier gas are dilute gases such as helium or argon, nitrogen, carbon dioxide, alcohols such as methanol, carbonyl compounds such as acetone, saturated hydrocarbons such as methane, ethane, propane, butane or cyclohexane, and unsaturated hydrocarbons such as ethylene, acetylene, propylene or benzene.

In order to obtain the β,γ-unsaturated aldehyde in a high yield by the process of this invention, it is desirable to select the catalyst and the reaction conditions so that the conversion falls within a suitable range. When the conversion is high, the amount of the by-product saturated alcohol increases, and the amount of an α,β-unsaturated aldehyde often increases. Although the selectivity of the β,γ-unsaturated aldehyde is higher with lowwer conversions, the suitable conversion for the process of this invention is 15 to 60%, especially 25 to 55%.

Thus, the process of this invention makes it possible to prepare β,γ-unsaturated aldehydes of formula (II) from the corresponding β,γ-unsaturated alcohols of formula (I) in high yields. In contrast, the process disclosed in U.S. Pat. No. 2,042,220 is directed to the preparation of unsaturated aldehydes by contacting unsaturated alcohols and oxygen with copper at high temperatures thereby to oxidize the alcohols. Example 2 of this United States Patent describes the reaction of 2-methyl-1-buten-4-ol which is a β,γ-unsaturated alcohol. We traced this reaction using the reaction conditions described there, and the results are shown hereinbelow as a comparison (Referential Example 3). The results show that the main reaction product is 2-methyl-2-buten-4-al which is an α,β-unsaturated aldehyde, the selectivity of the β,γ-unsaturated aldehyde is low, and the activity of the catalyst is reduced very rapidly and the conversion after reaction for 3 to 6 hours is only 4%. In contrast, according to one embodiment of the process of this invention as will be shown later on in which the reaction was performed in the presence of steam at the same temperature and using the same catalyst as used in the above comparative example, the conversion after reaction for 48 to 72 hours is about 43%.

Cooling the reaction product obtained above by the process of this invention affords an oily product. When steam is used in the reaction of this invention, cooling the reaction product gives the above oily product and an aqueous phase as separate phases. The oily product is therefore separated and recovered by a known method. Since the aqueous phase obtained still contains a small amount of the reaction product and the unreacted β,γ-unsaturated alcohol dissolved therein, it is desirably recycled to the reaction systemm to use it again in the dehydrogenation reaction in accordance with this invention. [Purification of Crude β,γ-Unsaturated Aldehydes]

The oily reaction product obtained by the dehydrogenation reaction in accordance with this invention contains, in addition to the β,γ-unsaturated aldehyde of formula (II), byproducts such as (A) the unreacted β,γ-unsaturated alcohol of formula (I), (B) an α,β-unsaturated aldehyde of the formula

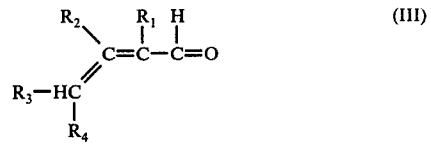

wherein $R_1$, $R_2$, $R_3$ and $R_4$ are the same as defined in formula (I), and (C) a saturated aldehyde of the formula

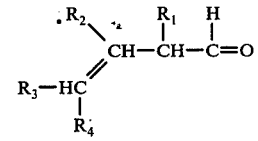

wherein $R_1$, $R_2$, $R_3$ and $R_4$ are the same as defined in formula (I).

Of these by-products, the unreacted unsaturated alcohol (A) and the α,β-unsaturated aldehyde (B) can be separated from the β,γ-unsaturated aldehyde as a main reaction product by distillation since there is an appreciable difference in boiling point. However, since the saturated aldehyde (C) has a boiling point very close to that of the desired reaction product, it is extremely difficult, and virtually impossible, to separate the saturated aldehyde from the β,γ-unsaturated aldehyde by distillation.

For example, the reaction product obtained by dehydrogenation of 2-methyl-1-buten-4-ol as the β,γ-unsaturated alcohol of formula (I) contains by-product isovaleraldehyde (IVA) corresponding to the saturated aldehyde (C) in addition to 2-methyl-1-buten-4-al (MBA) as the final product. The boiling points of these products are very close to each other as shown below.

| Products | Standard boiling point (760 mmHg) |
| --- | --- |
| MBA | 96° to 96 C. |
| IVA | 94 to 95° C. |

Our investigations, however, led to the discovery that by distilling in the presence of water a composition at least containing a β,γ-unsaturated aldehyde of the formula

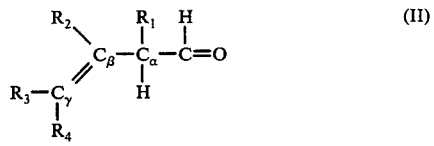

wherein $R_1$, $R_2$ and $R_3$ are identical or different and represent a hydrogen atom or a methyl group, and $R_4$ is a hydrogen atom or a linear or cyclic saturated or unsaturated hydrocarbon residue containing 1 to 6 carbon atoms, and a saturated aldehyde of the formula

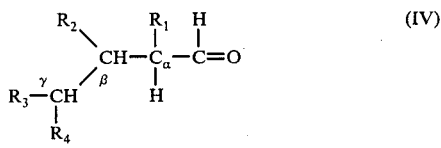

wherein $R_1$, $R_2$, $R_3$ and $R_4$ are the same as defined in formula (II),
the above $\beta,\gamma$-unsaturated carbonyl compound can be separated from the above $\beta,\gamma$-saturated carbonyl compounds.

Furthermore, the unreacted $\beta,\gamma$-unsaturated alcohol (A) and the $\alpha,\beta$-unsaturated aldehyde (B) contained in the hydrogenation reaction product of this invention also have boiling points close to each other, and are therefore extremely difficult to separate from each other by distillation. The use of the distilling method using water makes it possible to separate the unreacted $\alpha,\beta$-unsaturated alcohol (A) and the $\alpha,\beta$-unsaturated aldehyde (B) from each other, and in addition to separate these two compounds (A) and (B) completely from the desired reaction product $\beta,\gamma$-unsaturated aldehyde of formula (II).

Accordingly, if the distilling method in accordance with this method is applied to the product obtained by the dehydrogenation in accordance with this invention, not only the unreacted $\beta,\gamma$-unsaturated alcohol (A) but also other by-products such as (B) and (C) can be well separated from the final desired product, and thus, the purified $\beta,\gamma$-unsaturated aldehyde of formula (II) can be recovered easily.

The amount of water copresent in the distilling method of this invention can be varied over a wide range according to the distilling temperature, the composition of the raw material, etc. Usually, the suitable amount of water is 0.02 to 50 parts by weight, especially 0.05 to 20 parts by weight, per part by weight of the starting mixture. When the amount of water exceeds the upper limit of this range, the total amount of the liquid to be treated increases remarkably, and the diameter of the distillation tower must be greatly increased, which in turn results in an increased cost of equipment. On the other hand, if the amount of water is smaller than the lower limit of the above-specified range, the effect of separating the $\beta,\gamma$-unsaturated aldehyde of formula (II) from the saturated aldehyde of formula (IV) is reduced, and the separation of them by distillation becomes substantially impossible.

Water may be fed to the starting miture before placing it in a distillation tower, or to a part half-way in the distillation tower or to a still at the bottom of the tower. When the distillate is cooled, it separates into a oily phase and an aqueous phase. Since the aqueous phase contains a part of the unreacted $\beta,\gamma$-unsaturated alcohol dissolved therein, it is advantageous to separate the oily product from the aqueous phase and to recycle the aqueous phase to a suitable position in the distillation tower.

However, in performing the separating process of this invention, the available procedure is not limited to that exemplified above, but any procedure by which water is present in the distillation system can be employed.

The distillation temperature used in this invention is usually 10° to 200° C., preferably 20° to 180° C., especially preferably 20° to 150° C. However, since the thermal stability of the $\beta,\gamma$-unsaturated aldehyde of formula (II) is not so good, it sometimes decomposes at a temperature of more than 180° C., especially more than 200° C. and care must therefore be taken in this regard.

The pressure used in the distillation can be normal atmospheric pressure or an elevated or reduced pressure. The pressure drop is determined by the type of the distillation tower, but in short, it is desirable to set the operating pressure so as to provide the above distillation temperature.

When the above distilling process of this invention is applied to the dehydrogenation reaction product obtained by the process of this invention, a saturated aldehyde of formula (IV) first distills out, and then a $\beta,\gamma$-unsaturated aldehyde of formula (II), than an $\alpha,\beta$-unsaturated aldehyde of formula (III), and finally the unreacted $\beta,\gamma$-unsaturated alcohol of formula (I).

When an oxidizing gas is present in the distillation system in accordance with this invention, the $\beta,\gamma$-unsaturated aldehyde of formula (II) and the saturated aldehyde of formula (IV) sometimes decompose, and therefore, an inert gas such as nitrogen, helium or argon may be caused to be present in the distillation system.

The distillation can be performed using various distilling devices such as those of the plate type, packed type or liquid film type.

Furthermore, the distillation can be carried out either batchwise or continuously. The distillate obtained by the distillation of this invention forms two liquid phases, an organic phase and an aqueous phase. The organic phase can be directly sent to a subsequent step. The aqueous phase separated may be recycled to the distillation tower, or discarded as such. [Preparation of $\beta,\gamma$-Unsaturated Alcohols as Starting Material]

The $\beta,\gamma$-unsaturated alcohol of formula (I) used as a starting material in the dehydrogenation reaction of this invention may be those prepared by any methods.

However, our investigations have shown that $\beta,\gamma$-unsaturated alcohols of the formula

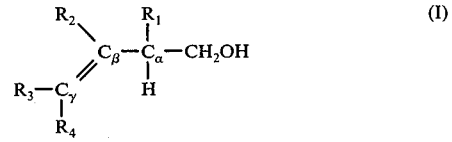

wherein $R_2$, $R_3$ and $R_4$ are identical or different and represent a hydrogen atom or a methyl group, and $R_1$ is a hydrogen atom or a linear or cyclic saturated or unsaturated hydrocarbon residue containing 1 to 6 carbon atoms,
can be advantageously prepared by reacting olefins of the formula

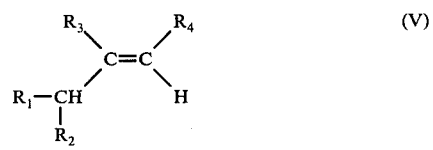

wherein $R_1$, $R_2$, $R_3$ and $R_4$ are the same as defined in formula (I),
with formaldehyde or a derivative capable of forming formaldehyde at a temperature of 180° to 400° C. in the absence of a solvent or in the presence of a non-aqueous organic solvent after preheating the formaldehyde or the derivative to a temperature of 80° to 150° C.

Methods have already been known to prepare β,γ-unsaturated alcohols by reacting olefins with formaldehyde or its polymer. For example, U.S. Pat. No. 2,335,027 and Journal of the American Chemical Society, Vol. 77, pages 4666 to 4668 (1955) disclose the reaction of diisobutylene or β-pinene with formaldehyde; Journal of the American Chemical Society, Vol. 77 (1955), pages 78-80 discloses the reaction of isobutylene with formaldehyde; and U.S. Pat. No. 2,308,192 discloses the same reaction in which trioxymethylene is used. Furthermore, German DAS 1,618,098 discloses in Example 6 the synthesis of 3-methylbuten-(3)-1-ol by reacting isobutylene with trioxane using tetrahydrofuran as a diluent, but the selectivity is only 48%.

Our investigations show that when a olefin is mixed with an aldehyde and the mixture is heated merely to the desired reaction temperature in an attempt to produce an unsaturated alcohol, the unsaturated alcohol is obtained only in a selectivity of less than about 50% as in the above citations, and that when an aldehyde polymer is used as a source of the aldehyde, a sandlike solid colored brown or black is produced in great quantities as a by-product, which sometimes causes blockage of the pipes and thus a failure of continuous operation.

We furthered our investigations so as to remove such defects, and found that when formaldehyde or a derivative capable of forming an aldehyde, such as a formaldehyde polymer, is pre-heated to a certain predetermined temperature prior to the reaction, the unsaturated alcohol can be obtained in a high selectivity of, say, more tha 70%.

The olefin of formula (V) used as a starting material in the above process may be any olefin corresponding to the β,γ-unsaturated alcohol of formula (I). Isobutylene is especially preferred.

The derivative capable of forming formaldehyde may be any derivative, such as a formaldehyde polymer, which can form formaldehyde under the reaction conditions of this invention. Any formaldehyde or its derivative capable of forming formaldehyde can be used in the present invention, but the process of this invention can be especially advantageously performed by using a formaldehyde polymer. Examples of preferred formaldehyde polymers are trioxane, tetraoxymethylene, and paraformalehyde. The use of paraformaldehyde is especially advantageous. The paraformaldehyde has good stability and is easy to handle. Furthermore, it is easily available as a commercial article, and can be directly used in the reaction of this invention.

The molar ratio of the olefin and the formaldehyde closely affects the yield of the desired unsaturated alcohol. Accordingly, it is preferred to adjust the ratio of the olefin (mols) to the aldehyde (1 mol) to at least 2n, as shown in formula (I) below. The symbol $n$ here means the number of double bonds contained in the olefin, and especially preferably, the double bonds are such that at least one hydrogen atom is bonded to at least one of the carbon atoms adjacent to the carbon atoms of the double bond.

$$\frac{\text{Mols of olefin}}{\text{Mols of formaldehyde}} \geq 2n \qquad (1)$$

When a formaldehyde polymer is used, its molar amount is regarded as containing the mols of an aldehyde which is formed by its decomposition. For example, trioxane is dealt with as 3 mols of formaldehyde.

The preferred olefin/aldehyde ratio is at least 3n, especially at least 4n, and especially advantageously 5n to 18n. This molar ratio adjustment permits unsaturated alcohols of high purity to be obtained in very high yields.

When the olefin/formaldehyde molar ratio is less than 2n, the amounts of by-products are very large, and the resulting unsaturated alcohols have low purity, and the yield of the alcohols is very low. On the other hand, there is no particular upper limit to the above molar ratio, but usually, it is desirable that this molar ratio is up to 100 $n$, preferably up to 50 $n$. The use of too much olefins is economically disadvantageous.

In the process of this invention, formaldehyde or its polymer is pre-heated to a temperature of 80° to 150° C. If the pre-heating temperature is lower than 80° C., no effect is obtained, and the selectivity does not reach 50%. When the preheating temperature exceeds 150° C., the selectivity does not reach 50%. The preferred pre-heating temperature is 100° to 140° C., especially 110 to 135° C. The pre-heating time, although varying according to the pre-heating temperature, is usually 1 minute to several hours, preferably 5 to 120 minutes, and especially preferably 10 to 60 minutes.

If a non-aqueous organic solvent is used, the preheating of the aldehyde or its polymer may be carried out in this solvent, or in a mixture of the aldehyde or its polymer with the olefin, or in a mixture of the aldehyde or polymer, or the olefin and the solvent. Especially advantageously, the formaldehyde or its polymer is preheated together with the olefin, and then the mixture is further heated to the desired reaction temperature for further reaction.

Various types of pre-heating devices can be used. For example, when the formaldehyde or its polymer is preheated together with the solvent and/or olefin, a stirred vessel, a mono-tube type heat-exchanger, or a multi-tube heat exchanger can be employed.

The reaction temperature used in the above process is higher than 180° and up to 400° C., especially 200° to 340° C. The residence time or reaction time is affected mainly by the reaction temperature, but usually 1 minute to 30 hours, preferably 5 minutes to 10 hours, especially preferably 10 minutes to 5 hours. The reaction pressure is one sufficient to maintain the reaction mixture in the liquid phase, and is determined mainly by the reaction temperature, and the molar ratio of olefin to formaldehyde or a derivative capable of forming the formaldehyde.

The intended unsaturated alcohols can be obtained by performing the reaction in the substantial absence of a catalyst, and this procedure is advantageous. However, there is no reason why a catalyst should not be used.

The reaction of this invention can be performed in the absence of solvent, as mentioned above, but non-aqueous organic solvents may be used. Examples of such non-aqueous organic solvents are halogenated hydrocarbons such as chloroform or 1,2-dichloroethane, ethers such as diethyl ether, tetrahydrofuran, para-dioxane or tetrahydropyran, fatty acids such as acetic acid, esters such as ethyl acetate, aliphatic hydrocarbons such as hexane, octane or n-heptane, alicyclic hydrocarbons such as cyclohexane, aromatic hydrocarbons such as benzene, toluene or xylene, and dioxanes such as p-dioxane.

Especially advantageously, the process of this invention is carried out using a non-aqueous solvent.

The process of this invention can be performed either batchwise or continuously.

The following Examples illustrate the processes of this invention without any intention of limiting the invention thereby.

EXAMPLE 1 AND REFERENTIAL EXAMPLE 1

This Example shows that the process of this invention was performed using copper catalysts having various specific surface areas. The preparation of the catalysts and their forms were as follows:

A. Preparation of Catalysts (i) Catalyst used in Example 1-(1)

This catalyst is a rod-like copper oxide with a diameter of 0.8 mm and a length of 5 to 10 mm which was obtained by igniting rod-like metallic copper in air.

(ii) Catalyst used in Example 1-(2)

A net-like copper oxide, cut to a size of 2 to 8 mm, obtained by calcining a copper screen of 80 mesh in air at 800° C. for 3 hours.

(iii) Catalyst used in Example 1-(3)

This catalyst was obtained by molding a 150-mesh copper powder under pressure into pellets with a diameter of 6 mm and a thickness of 3 mm and then calcining the pellets in air at 800° C. for 5 hours.

(iv) Catalyst used in Example 1-(4)

This catalyst was prepared by calcining a 150-mesh copper powder in air at 800° C. for 3 hours, and then molding the calcined powder into pellets having a diameter of 6 mm and a thickness of 3 mm.

(v) Catalyst used in Example 1-(5)

This catalyst was obtained by calcining a 100-mesh copper powder in air at 800° C. for 3 hours, and molding the powder under pressure into pellets having a diameter of 6 mm and a thickness of 3 mm.

(vi) Catalyst used in Referential Example 1-(1)

This catalyst was prepared by calcining cupric hydroxide in air at 600° C. for 3 hours to convert it to copper oxide, and then molding it under pressure into pellets having a diameter of 6 mm and a thickness of 3 mm.

(vii) Catalyst used in Referential Example 1-(2)

This catalyst was prepared by calcining basic copper carbonate in air at 500° C. for 3 hours, and molding the resulting copper oxide under pressure into pellets having a diameter of 6 mm and a thickness of 3 mm.

B. Reaction

The reaction in Example 1-(1) was as follows:

The rod-like catalyst (20 g=9 cc) was packed in a glass reaction tube with an inside diameter of 28 mm, and glass balls were packed on top of the catalyst layer to provide an evaporating-preheating layer. The entire reaction tube was heated externally by an electric oven. While maintaining the temperature of the catalyst layer at 350° C., a gaseous mixture of hydrogen and nitrogen was fed into the catalyst layer to reduce the copper oxide catalyst to metallic copper.

Then, while maintaining the temperature of the reaction tube at 240° C., 3.0 g/hr of 2-methyl-1-buten-4-ol and 10.8 liters/hr (calculated on the basis of standard condition of nitrogen) were fed from the end of the reactor. The reaction product which distilled out from the lower end of the reaction tube was collected. After a lapse of 3 hours, 8.7 g of the reaction product was obtained. This reaction product was quantitatively analyzed by gas-chromatography, and found to contain 2.07 g of unreacted 2-methyl-1-buten-4-ol, 1.42 g of 2-methyl-1-buten-4-al ($\beta,\gamma$-unsaturated aldehyde), 1.28 g of 2-methyl-2-buten-4-al ($\alpha,\beta$-unsaturated aldehyde), 3.46 g of isovaleraldehyde (saturated aldehyde), and 0.35 g of isoamyl alcohol (saturated alcohol). This result corresponded to a conversion of 77%, a 2-methyl-1-buten-4-al selectivity of 21%, a 2-methyl-2-buten-4-al selectivity of 19%, an isovaleraldehyde selectivity of 50%, and an isoamyl alcohol selectivity of 5%.

The WHSV (the amount of the starting material fed per unit weight of the catalyst per hour) was 0.15 g/g.hr, and the concentration of 2-methyl-1-buten-4-al was 6.7% by volume.

The reaction was carried out further, and the following results were obtained after performing the reaction for 3 to 6 hours.

| Conversion | 52% |
|---|---|
| Selectivity of 2-methyl-1-buten-4-al | 45% |
| Selectivity of 2-methyl-2-buten-4-al | 30% |
| Selectivity of isovaleraldehyde | 21% |
| Selectivity of isoamyl alcohol | 1% |

The results of reactions conducted for 6 to 9 hours, 9 to 12 hours, and 12 to 15 hours, respectively, are shown in Table 1(b).

Examples 1-(2) to 1-(5) and Referential Examples 1-(1) and 1-(2) were also performed in the same way as in Example 1-(1), and the results are shown in Table 1(b).

The specific surface area of the catalyst shown in Table 1(a) was measured by means of a softometer (Perkin Elmer Shell Model 212D, made by Perkin Elmer) after reducing the copper oxide catalyst with hydrogen at 250° C. This measurement method is a modification of the BET method.

Table 1 (a)

| | Specific surface area of catalyst and the reaction conditions | | | | | | |
|---|---|---|---|---|---|---|---|
| Run No. | Specific surface area ($m^2/g$) | Amount of catalyst (g.(cc.)) | Amount of 2-methyl-1-buten-4-ol (g/hr) | Carrier gas | Concentration of 2-methyl-1-buten-4-ol (vol.%) | WHSV (g/g.hr) | Reaction temperature (° C) |
| Example 1-(1) | 0.10 | 20(9) | 3.0 | $N_2$ | 6.7 | 0.15 | 240 |
| "1-(2) | 0.14 | 20(17) | 3.0 | $N_2$ | 6.7 | 0.15 | 240 |
| "1-(3) | 0.24 | 20( 6) | 3.0 | $N_2$ | 6.7 | 0.15 | 240 |
| "1-(4) | 0.43 | 20( 7) | 3.0 | $N_2$ | 6.7 | 0.15 | 240 |
| "1-(5) | 0.92 | 10(4.5) | 3.0 | $N_2$ | 6.7 | 0.30 | 240 |
| Referential | | | | | | | |

Table 1 (a)-continued

Specific surface area of catalyst and the reaction conditions

| Run No. | Specific surface area (m²/g) | Amount of catalyst (g.(cc.)) | Amount of 2-methyl-1-buten-4-ol (g/hr) | Carrier gas | Concentration of 2-methyl-1-buten-4-ol (vol.%) | WHSV (g/g.hr) | Reaction temperature (°C) |
|---|---|---|---|---|---|---|---|
| Example 1-(1) | 1.8 | 10( 4) | 3.0 | $N_2$ | 6.7 | 0.30 | 240 |
| "1-(2) | 3.4 | 5(3.5) | 3.0 | $N_2$ | 6.7 | 0.60 | 220 |

Table 1 (b)

Results of Reaction

| Run No. | Reaction time (hr) | Conversion (%) | Selectivity 2-Methyl-1-buten-4-al (%) | 2-Methyl-2-buten-4-al (%) | Isovaler-aldehyde (%) | Isoamyl alcohol (%) |
|---|---|---|---|---|---|---|
| Example 1-(1) | 0 – 3 | 77 | 21 | 19 | 50 | 5 |
|  | 3 – 6 | 52 | 45 | 30 | 21 | 1 |
|  | 6 – 9 | 41 | 56 | 24 | 17 | 0 |
|  | 9 – 12 | 34 | 61 | 22 | 15 | 0 |
|  | 12 – 15 | 31 | 65 | 21 | 13 | 0 |
| Example 1-(2) | 0 – 3 | 82 | 20 | 21 | 54 | 3 |
|  | 3 – 6 | 64 | 38 | 25 | 35 | 1 |
|  | 6 – 9 | 54 | 49 | 29 | 21 |  |
| Example | 9 – 12 | 47 | 55 | 25 | 19 | 0 |
|  | 12 – 15 | 43 | 59 | 24 | 16 | 0 |
| Example 1-(3) | 0 – 3 | 70 | 27 | 24 | 38 | 7 |
|  | 3 – 6 | 42 | 52 | 30 | 16 | 0 |
|  | 6 – 9 | 32 | 64 | 24 | 11 | 0 |
|  | 9 – 12 | 27 | 67 | 20 | 13 | 0 |
|  | 12 – 15 | 24 | 72 | 18 | 9 | 0 |
| Example 1-(4) | 0 – 3 | 62 | 35 | 27 | 33 | 2 |
|  | 3 – 6 | 48 | 49 | 28 | 20 | 0 |
|  | 6 – 9 | 40 | 58 | 23 | 18 | 0 |
|  | 9 – 12 | 35 | 60 | 23 | 15 | 0 |
|  | 12 – 15 | 32 | 64 | 22 | 14 | 0 |
| Example 1-(5) | 0 – 3 | 68 | 22 | 28 | 41 | 3 |
|  | 6 – 9 | 48 | 36 | 36 | 26 | 0 |
|  | 12 – 15 | 37 | 54 | 26 | 20 | 0 |
| Referential Example 1-(1) | 0 – 3 | 85 | 14 | 36 | 35 | 9 |
|  | 6 – 9 | 63 | 21 | 42 | 30 | 3 |
|  | 12 – 15 | 51 | 24 | 45 | 29 | 0 |
|  | 24 – 27 | 38 | 32 | 47 | 20 | 0 |
| Referential Examle 1-(2) | 0 – 3 | 90 | 5 | 23 | 53 | 11 |
|  | 6 – 9 | 58 | 12 | 47 | 36 |  |
|  | 12 – 15 | 45 | 16 | 52 | 28 | 1 |
|  | 24 – 27 | 36 | 19 | 52 | 27 | 0 |

Example 2 and Referential Example 2

This Example shows experiments with varying reaction temperatures.

The same procedure as in Example 1-(1) was repeated using the same catalyst as used in Example 1-(1). The amount of the catalyst was 20 g (9 cc); the rate of feeding 2-methyl-1-buten-4-ol was 3.0 g/hour; the carrier gas was $N_2$; the concentration of 2-methyl-1-buten-4-ol was 6.7% by volume; and WHSV was 0.15 g/g.hr. The reaction was carried out under the above conditions at varying temperatures. The results are shown in Table 2.

Table 2

| Run No. | Reaction temperature (°C) | Reaction time (hr) | Conversion (%) | Selectivity (%) 2-Methyl-1-buten-4-al | 2-Methyl-2-buten-4-al | Isovaler-aldehyde | Isoamyl alcohol |
|---|---|---|---|---|---|---|---|
| Example 2-(1) | 200 | 0 – 3 | 35 | 47 | 14 | 32 | 0 |
|  |  | 3 – 6 | 24 | 67 | 18 | 14 | 0 |
|  |  | 6 – 9 | 20 | 70 | 17 | 12 | 0 |
| Example 2-(2) | 220 | 0 – 3 | 70 | 31 | 24 | 38 | 5 |
|  |  | 3 – 6 | 48 | 45 | 25 | 30 | 0 |
|  |  | 6 – 9 | 37 | 62 | 19 | 19 | 0 |
|  |  | 9 – 12 | 30 | 66 | 17 | 16 | 0 |
|  |  | 12 – 15 | 27 | 69 | 16 | 15 | 0 |
| Example 2-(3) | 260 | 0 – 3 | 66 | 23 | 30 | 39 | 3 |
|  |  | 3 – 6 | 30 | 51 | 30 | 17 | 0 |
| Example 2-(4) | 280 | 0 – 3 | 45 | 20 | 30 | 37 | 4 |
|  |  | 3 – 6 | 21 | 40 | 33 | 25 | 0 |
| Referential Example 2-(1) | 320 | 0 – 3 | 18 | 15 | 39 | 28 | 6 |
|  |  | 3 – 6 | 5 | 27 | 51 | 14 | 0 |

Referential Example 3

This Example shows a reaction performed under the reaction conditions described in Example 2 of United States Patent 2,042,220.

Using the same catalyst as used in Example 1-(1), and the same reaction apparatus and method (300° C.) as used in Example 1-(1) 3.0 g/hr of 2-methyl-1-buten-4-ol and 1.8 liters/hour of air were fed. The reaction product was quantitatively analyzed in the same way as in Example 1-(1). The results are shown in Table 3.

Table 3

| Reaction time (hr) | Conversion (%) | Selectivity (%) | | | |
|---|---|---|---|---|---|
| | | 2-Methyl-1-buten-4-al | 2-Methyl-2-buten-4-al | Isovaleraldehyde | Isoamyl alcohol |
| 0 to 3 | 55 | 8 | 36 | 12 | 0 |
| 3 to 6 | 4 | 11 | 12 | 3 | 0 |

EXAMPLE 3

In this Example, the process of this invention was performed at reduced pressure.

A stainless steel reaction tube with an inside diameter of 24 mm was packed with 60 g (51 cc) of the same catalyst as used in Example 1-(2), and reduced with hydrogen at 250° C. The pressure was adjusted to 50 mmHg, and 2-methyl-1-buten-4-ol was fed at a rate of 3.0 g/hour at a temperature of 240° C. without using a carrier gas. The resulting product was quantitatively analyzed in the same way as in Example 1-(1). The results are shown in Table 4. The WHSV was 0.05 g/g.hr.

Table 4

| Reaction time (hours) | Conversion (%) | Selectivity (%) | | |
|---|---|---|---|---|
| | | 2-Methyl-1-buten-4-al | 2-Methyl-2-buten-4-al | Isovaleraldehyde |
| 0 to 6 | 54 | 38 | 32 | 16 |
| 6 to 12 | 36 | 44 | 37 | 13 |
| 12 to 18 | 32 | 52 | 33 | 11 |

Example 4

In this Example, the concentration of a carrier gas was varied.

The same procedure as in Example 1-(1) was repeated using the same catalyst as used in Example 1-(2). The reaction conditions and the results are shown in Tables 5(a) and 5(b).

Table 5(a)

| Example | Amount of catalyst (g) | Reaction conditions | | | | |
|---|---|---|---|---|---|---|
| | | 2-Methyl-1-buten-4-ol (g/hr) | $N_2$ (l/hr) | WHSV (g/g.hr) | Reaction temperature (° C.) | 2-Methyl-1-buten-4-ol (vol.%) |
| 4-(1) | 40 | 3.0 | 23.6 | 0.075 | 240 | 3.2 |
| 4-(2) | 20 | 3.0 | 7.0 | 0.150 | 240 | 10 |
| 4-(3) | 20 | 3.0 | 4.4 | 0.150 | 240 | 15 |

Table 5 (b)

| Run No. | Reaction time (hr) | Conversion (%) | Selectivity (%) | | | |
|---|---|---|---|---|---|---|
| | | | 2-Methyl-1-buten-4-al | 2-Methyl-2-buten-4-al | Isovaleraldehyde | Isoamyl alcohol |
| Example 4-(1) | 0 – 6 | 62 | 36 | 14 | 42 | 5 |
| | 6 – 12 | 28 | 55 | 19 | 25 | 6 |
| | 12 – 18 | 16 | 70 | 16 | 13 | 0 |
| Example 4-(2) | 0 – 6 | 80 | 21 | 21 | 47 | 8 |
| | 6 – 12 | 60 | 41 | 27 | 31 | 0 |
| | 12 – 18 | 50 | 49 | 26 | 24 | 0 |
| | 18 – 24 | 45 | 52 | 26 | 21 | 0 |
| | 24 – 30 | 40 | 57 | 24 | 18 | 0 |
| Example 4-(3) | 0 – 6 | 87 | 15 | 16 | 48 | 10 |
| | 6 – 12 | 62 | 31 | 24 | 38 | 0 |
| | 12 – 18 | 53 | 38 | 25 | 32 | 0 |
| | 18 – 24 | 49 | 43 | 25 | 29 | 0 |
| | 24 – 30 | 46 | 46 | 28 | 23 | 0 |

EXAMPLE 5

In this Example, the process of this invention was performed using a gaseous mixture of acetone and nitrogen and a gaseous mixture of benzene and nitrogen as a carrier gas.

The same procedure as in Example 1-(1) was repeated using the same catalyst as used in Example 1-(2). Acetone or benzene used as the carrier gas was added dropwise from the upper end of the reaction tube in the same way as in the case of feeding the starting 2-methyl-1-buten-4-ol.

The reaction conditions and the results are shown in Table 6.

Table 6(a)

| Run No. | Amount of catalyst g (cc) | Amount of 2-methyl-1-buten-4-ol fed (g/hr) | Amount of carrier fed | | Concentration of 2-methyl-buten-4-ol (vol %) | WHSV (g/g.hr) | Reaction temperature (° C) |
|---|---|---|---|---|---|---|---|
| | | | (l/hr) | (g/hr) | | | |
| Example 5-(1) | 20 (17) | 3.0 | $N_2$ 5.44 | Benzene 18.9 | 6.7 | 0.15 | 240 |
| Example 5-(2) | 20 (17) | 3.0 | $N_2$ 5.44 | Acetone 11.1 | 6.7 | 0.15 | 240 |

Table 6(b)

| Example | Reaction time (hr) | Conversion % | Selectivity % | | | |
|---|---|---|---|---|---|---|
| | | | 2-Methyl-1-buten-4-al | 2-Methyl-2-buten-4-al | Isovaleraldehyde | Isoamyl alcohol |
| 5-(1) | 0 – 6 | 93 | 15 | 15 | 55 | 5 |
| | 24 – 30 | 44 | 59 | 22 | 17 | 0 |
| | 48 – 54 | 18 | 73 | 18 | 9 | 0 |
| 5-(2) | 0 – 6 | 68 | 36 | 25 | 35 | 2 |
| | 24 – 30 | 42 | 57 | 26 | 16 | 0 |
| | 48 – 54 | 25 | 69 | 20 | 10 | 0 |

EXAMPLE 6

In this Example, the process of this invention was carried out using 2-methyl-1-buten-4-ol as a starting material.

A. Preparation of Catalyst (i) The catalyst used in Example 6-(1) was prepared by calcining a 80-mesh net of copper in air at 800° C. for 3 hours. and cutting the net-like copper oxide to a size of 2 to 8 mm. The catalyst was converted to metallic copper by hydrogenation with hydrogen at 250° C. The specific surface area, as determined by using a softometer (Perkin Elmer Shell Model 212D, made by Perkin Elmer), of the catalyst was 0.14 m²/g.

(ii) The catalyst used in Example 6-(2) was a rod-like copper oxide having a diameter of 0.8 mm and a length of 5 to 10 mm obtained by igniting rod-like metallic copper in air. The copper oxide was reduced with hydrogen, and its specific surface area, measured in the same manner as above, was 0.10 m²/g.

B. Reaction

The reaction in Example 6-(1) was performed as follows:

200 g (141 cc) of the net-like copper oxide catalyst was packed in a glass reaction tube with an inside diameter of 28 mm, and glass balls were pakced on top of the catalyst layer to provide an evaporating-preheating layer. The entire reaction tube was then heated externally by an electric oven. While maintaining the catalyst layer at a temperature of 250° C., a gaseous mixture of hydrogen and nitrogen was fed into the catalyst layer to reduce the copper oxide to metallic copper.

Then, while maintaining the reaction tube at 250° C., and 20 g/hr of 2-methyl-1-buten-4-ol and 38 g/hr of water were fed from the top end of the reaction tube. The reaction product that distilled out from the lower end of the reaction tube was collected. The reaction product which was obtained after a lapse of 24 hours from the initiation of the reaction and weighed 1368 g was separated into an oily phase and an aqueous phase.

Each of the phases was quantitatively analyzed by gas-chromatography. The results were as follows:

| | |
|---|---|
| Unreacted 2-methyl-1-buten-4-ol | 146.6 g (1.705 mols) |
| 2-Methyl-1-buten-4-al | 95.6 g (1.138 mols) |
| 2-Methyl-2-buten-4-al | 130.7 g (1.556 mols) |
| Isovaleroaldehyde | 78.3 g (0.910 mol) |
| Isoamyl alcohol | 10.0 g (0.113 mol) |

The amount of the starting 2-methyl-1-buten-4-ol fed in the course of 24 hours was 473 g (5.50 mols), and the selectivity of the 2-methyl-1-buten-4-al was 30%. Also the selectivity was 41% for 2-methyl-2-buten-4-al, 24% for isovaleraldehyde, and 3% for the isoamyl alcohol.

The WHSV (the weight of the 2-methyl-1-buten-4-ol per unit weight of the catalyst per hour) was 0.10 l/hr. The concentration of 2-methyl-1-buten-4-ol fed was 9.9% by volume, and the molar ratio of the 2-methyl-1-buten-4-ol to water was 9.1.

The reaction was performed further under the same conditions, and the results are shown in Table 7.

Example 6-(2) was performed using 300 g (99 cc) of the above rod-like copper oxide catalyst which had been reduced with hydrogen in the same way as in Example 6-(1). The results are also shown in Table 7.

Table 7

| Run No. | Reaction Conditions | | | | | | Results of Reaction | | | | | | |
|---|---|---|---|---|---|---|---|---|---|---|---|---|---|
| | Reaction temperature (°C) | WHSV (1/hr) | Concentration of 2-methyl-1-buten-4-ol (vol %) | Molar ratio of H₂O/2-methyl-1-buten-4-ol | | | Reaction time (hr) | | | | | | |
| | | | | | | | 0–24 | 24–48 | 48–72 | 72–96 | 96–120 | 120–144 | 144–158 |
| 6-(1) | 250 | 0.10 | 9.9 | 9.1 | | Conversion (%) | 69 | 64 | 57 | 51 | 45 | 42 | 33 |
| | | | | | Selectivity (%) | 2-Methyl-1-buten-4-al | 30 | 37 | 42 | 47 | 53 | 56 | 57 |
| | | | | | | 2-Methyl-2-buten-4-al | 41 | 38 | 37 | 36 | 36 | 34 | 35 |
| | | | | | | Isovaleroaldehyde | 24 | 21 | 18 | 15 | 11 | 10 | 8 |
| | | | | | | Isoamyl alcohol | 3 | 3 | 2 | 1 | 0 | 0 | 0 |
| 6-(2) | 250 | 0.066 | 9.9 | 9.1 | | Conversion (%) | 74 | 59 | 52 | 48 | 42 | 38 | — |
| | | | | | Selectivity (%) | 2-Methyl-1-buten-4-al | 21 | 35 | 40 | 43 | 49 | 54 | — |
| | | | | | | 2-Methyl-2-buten-4-al | 35 | 45 | 44 | 44 | 42 | 40 | — |
| | | | | | | Isovaleroaldehyde | 31 | 17 | 13 | 11 | 7 | 6 | — |
| | | | | | | Isoamyl alcohol | 5 | 2 | 2 | 1 | 0 | 0 | — |

EXAMPLE 7

In this Example, the molar ratio of steam to 2-methyl-1-buten-4-ol was varied.

The process of this invention was performed at 260° C. using 30 g of the same rod-like copper oxide catalyst as used in Example 6-(2) and 3.0 g/hr of 2-methyl-1-buten-4-ol with WHSV of 0.10 l/hr.

The results are shown in Table 8.

In Example 7-(2), a nitrogen gas was additionally supplied, and the molar ratio between water and nitrogen gas was set at 1:1.

According to the results shown in Table 8, a greater part of the reaction product other than 2-methyl-1-buten-4-al and 2-methyl-2-buten-4-al was isovaleraldehyde, and in some cases, a small amount of isoamyl alcohol was formed in the early stage of the reaction.

Table 8

| Run No. | Reaction Conditions | | | | | Results of Reaction | | | | | | |
|---|---|---|---|---|---|---|---|---|---|---|---|---|
| | Reaction tempera-ture (° C) | WHSV (1/hr) | 2-Methyl-1-buten-4-ol (vol %) | Molar ratio of H$_2$O/2-methyl-1-buten-4-ol | Molar ratio of N$_2$/2-methyl-1-buten-4-ol | | | Reaction time (hr) | | | | |
| | | | | | | | | 0–24 | 24–48 | 48–72 | 72–96 | 96–120 |
| 7-(1) | 260 | 0.10 | 15.0 | 5.6 | 0 | Conversion (%) | | 70 | 49 | 43 | 39 | 37 |
| | | | | | | Selectivity (%) | 2-Methyl-1-buten-4-al | 22 | 39 | 45 | 46 | 53 |
| | | | | | | | 2-Methyl-2-buten-4-al | 35 | 41 | 42 | 42 | 38 |
| 7-(2) | 260 | 0.10 | 6.7 | 6.9 | 6.9 | Conversion (%) | | 64 | 39 | 31 | 25 | 20 |
| | | | | | | Selectivity (%) | 2-Methyl-1-buten-4-al | 30 | 54 | 58 | 67 | 78 |
| | | | | | | | 2-Methyl-2-buten-4-al | 42 | 38 | 36 | 31 | 20 |
| 7-(3) | 260 | 0.10 | 10.0 | 9.0 | 0 | Conversion (%) | | 62 | 47 | 40 | 37 | 35 |
| | | | | | | Selectivity (%) | 2-Methyl-1-buten-4-al | 31 | 48 | 49 | 54 | 55 |
| | | | | | | | 2-Methyl-2-buten-4-al | 45 | 39 | 41 | 38 | 38 |
| 7-(4) | 260 | 0.10 | 6.7 | 13.9 | 0 | Conversion (%) | | 56 | 41 | 37 | 35 | 33 |
| | | | | | | Selectivity (%) | 2-Methyl-1-buten-4-al | 40 | 50 | 55 | 59 | 60 |
| | | | | | | | 2-Methyl-2-buten-4-al | 40 | 41 | 38 | 35 | 33 |

EXAMPLE 8

The process of this invention was performed in the same way as in Example 7-(1) using 60 g of the same catalyst as used in Example 6-(2) [Example 8-(1)], 20 g of the same catalyst as used in Example 6-(1) [Example 8-(2)], and 20 g of the same catalyst as used in [Example 6-(2)], all of which catalysts had been reduced with hydrogen prior to use. The results are shown in Table 9.

Table 9

| Run No. | Reaction Conditions | | | | Results of Reaction | | | | | | |
|---|---|---|---|---|---|---|---|---|---|---|---|
| | Reaction tempera-ture (° C) | WHSV (1/hr) | 2-Methyl-1-buten-4-ol (vol %) | Molar ratio of H$_2$O/2-methyl-1-buten-4-ol | | | Reaction time (hr) | | | | |
| | | | | | | | 0–24 | 24–48 | 48–72 | 72–96 | 96–120 |
| 8-(1) | 240 | 0.05 | 6.7 | 13.9 | Conversion (%) | | 59 | 44 | 37 | 34 | 32 |
| | | | | | Selectivity (%) | 2-Methyl-1-buten-4-al | 37 | 45 | 52 | 55 | 59 |
| | | | | | | 2-Methyl-2-buten-4-al | 41 | 41 | 35 | 33 | 32 |
| 8-(2) | 260 | 0.15 | 6.7 | 13.9 | Conversion (%) | | 63 | 42 | 32 | 25 | 22 |
| | | | | | Selectivity (%) | 2-Methyl-1-buten-4-al | 38 | 49 | 60 | 61 | 69 |
| | | | | | | 2-Methyl-2-buten-4-al | 38 | 35 | 30 | 29 | 26 |
| 8-(3) | 300 | 0.15 | 10.0 | 9.0 | Conversion (%) | | 94 | 70 | 43 | 18 | — |
| | | | | | Selectivity (%) | 2-Methyl-1-buten-4-al | 11 | 28 | 48 | 55 | — |
| | | | | | | 2-Methyl-2-buten-4-al | 27 | 36 | 37 | 39 | — |

EXAMPLE 9

In this Example, the catalyst whose activity had been reduced through use was activated repeatedly to perform the process of this invention for long periods of time.

Preparation of Catalyst

Copper particles having a size of about 100 mesh and a flat form were heated with stirring in a stainless steel vessel to form copper oxide which was then calcined at 800° C. for 6 hours in air in an electric oven. The resulting powder was molded under pressure into pellets having a diameter of 5 mm and a thickness of 5 mm. The pellets were further calcined at 800° C. for 6 hours by an electric oven.

The resulting pellets were reduced with hydrogen at 250° C. The specific surface area of the metallic copper catalyst so prepared was 0.97 m$^2$/g.

30 g (11 ml.) of the pellets were packed in a glass reaction tube with an inside diameter of 28 mm, and glass balls were packed on top of the catalyst layer to provide an evaporating-preheating layer. The reaction tube was placed vertical, and entirely heated by an electric oven from outside. The temperature of the catalyst layer was maintained at 250° C., and hydrogen gas and water were fed from the upper part of the reaction tube to reduce the copper oxide catalyst to metallic copper.

| Reaction conditions and results | |
|---|---|
| Reaction temperature | 250° C. |
| Rate of 2-methyl-1-buten-4-ol fed | 3.0 g/hr |
| Rate of feeding water (steam) | 9.0 g/hr |
| WHSV | 0.1 l/hr |

The reaction was carried out under the above conditions. The catalyst with reduced activity was oxidized by supplying air and steam or nitrogen gas as a carrier gas, and then a reduced with hydrogen. The reaction was performed again under the above conditions using the activated catalyst. The reaction and the activation of the catalyst were repeated in this manner, and the results are shown in Table 10.

Table 10

| Number of activating cycle | Activating Conditions | | | | | | | | |
|---|---|---|---|---|---|---|---|---|---|
| | Oxidizing Conditions | | | | | Reducing Conditions | | | |
| | Temperature (° C) | Time (hr) | Rate of feeding gas (l/hr.) | Air (vol %) | Steam (vol %) | $N_2$ (vol %) | Temperature-Time (° C) | gas (hr) | Rate of feeding (vol (vol gas (l/hr.) %) | $H_2$ (vol %) | Steam % |

| Number of activating cycle | | | | | | | | | | | |
|---|---|---|---|---|---|---|---|---|---|---|---|
| 1 | 220 | 4 | 13 | 14 | 86 | 0 | 200 | 4 | 22 | 49 | 51 |
| 2 | 220 | 4 | 13 | 14 | 86 | 0 | 200 | 4 | 22 | 49 | 51 |
| 3 | 200 | 3 | 30 | 12 | 38 | 50 | 200 | 4 | 22 | 49 | 51 |
| 4 | 250 | 3 | 30 | 12 | 38 | 50 | 200 | 4 | 22 | 49 | 51 |

| Number of activating cycle | Conversion and selectivities | | Reaction time (days) | | | | |
|---|---|---|---|---|---|---|---|
| | | | 0-1 | 9-10 | 19-20 | 29-30 | 39-40 |
| 1 | Conversion (%) | | 75 | 44 | 39 | 35 | 33 |
| | Selectivity (%) | 2-Methyl-1-buten-4-al | 27 | 45 | 49 | 53 | 55 |
| | | 2-Methyl-2-buten-4-al | 39 | 45 | 43 | 42 | 40 |
| 2 | Conversion (%) | | 54 | 41 | 38 | 33 | 30 |
| | Selectivity (%) | 2-Methyl-1-buten-4-al | 45 | 51 | 54 | 57 | 58 |
| | | 2-Methyl-2-buten-4-al | 40 | 40 | 38 | 37 | 38 |
| 3 | Conversion (%) | | 52 | 40 | | 35 | |
| | Selectivity (%) | 2-Methyl-1-buten-4-al | 48 | 53 | | 58 | |
| | | 2-Methyl-2-buten-4-al | 39 | 39 | | 37 | |
| 4 | Conversion (%) | | 52 | 38 | 36 | | 34 |
| | Selectivity (%) | 2-Methyl-1-buten-4-al | 50 | 56 | 57 | | 59 |
| | | 2-Methyl-2-buten-4-al | 37 | 38 | 38 | | 38 |
| | Conversion (%) | | 53 | 39 | 38 | | 36 |
| | Selectivity (%) | 2-Methyl-1-buten-4-al | 51 | 57 | 58 | | 60 |
| | | 2-Methyl-2-buten-4-al | 35 | 36 | 35 | | 35 |

EXAMPLE 10

In this Example, 2-methyl-1-buten-4-ol was prepared and then dehydrogenated to form 2-methyl-1-buten-4-al which was then separated.

Synthesis of 2-methyl-1-buten-4-ol

A 5-liter autoclave equipped with a manometer a safety valve and an electromagnetically induced stirring device was charged with 120 g of commercially available paraformaldehyde (purity 97.7%), and then 2070 g of isobutylene was added from outside the autoclave after cooling the isobutylene with a dry ice-methanol cooling medium. The temperature inside the autoclave was elevated to 230° C. over the course of about 1 hour, and then the reaction was carried out for 1.5 hours. The autoclave was cooled, and at about 50° C., the unreacted isobutylene was purged. The product was withdrawn, and distilled at atmospheric pressure to afford 207 g of 2-methyl-1-buten-4-ol as a fraction boiling at 130° to 131° C.

Synthesis of 2-methyl-1-buten-4-al

Copper particles having a size of about 100 mesh and a flat form were heated with good stirring in a stainless steel vessel to form copper oxide which was then calcined in an electric oven at 800° C. for 18 hours in air. The resulting powder was molded under pressure into pellets having a diameter of 5 mm and a thickness of 5 mm.

The resulting pellets were reduced with hydrogen to metallic copper which had a specific surface area of 0.61 m²/g.

40 g (13 ml.) of the above pellets were packed into a glass reaction tube with an inside diameter of 28 mm, and glass balls were packed on top of the catalyst layer to provide an evaporating-preheating layer. The reaction tube was placed vertical, and the entire reaction tube was heated by an electric furnace from outside. While maintaining the catalyst layer at a temperature of 250° C., a hydrogen gas and water were fed from the upper part of the reaction tube to reduce the copper oxide catalyst to metallic copper.

While maintaining the temperature of the catalyst layer at 250° C., the 2-methyl-1-buten-4-ol and water were fed dropwise at a rate of 4.0 g/hr and 8.0 g/hr respectively from the upper part of the reaction tube. In the course of 6 to 7 days after the initiation of the reaction, 286 g of the reaction mixture was obtained.

Separation of 2-methyl-1-buten-4-al

This reaction mixture was separated into an oily phase and an aqueous phase. The oily phase was analyzed and found to contain 52.8% by weight of unreacted 2-methyl-1-buten-4-ol, 22.4% by weight of 2-methyl-1-buten-4-al, 15.2% by weight of 2-methyl-2-buten-4-al, 4.8% by weight of isovaleraldehyde and 4.8% by weight of water.

50 g of the oily phase and 10 g of water were placed in a still of a spinning band-type distillation tower (6 mm$\phi \times$ 1800 mml), and distilled at a pressure of 130 mmHg abs. and a reflux ratio of 30. During the distillation, water was fed continuously into the still at a rate of 8 cc/hr.

The distillate was separated into an oily phase and an aqueous phase, and a main fraction containing the constituents of the oily phase in high purity was collected. An intermediate fraction containing the constituents of the oily phase was further charged into the distillation tower, and the aqueous phase separated was recycled to the still at a rate of 8 cc/hour. The distillation was repeated under the above conditions. There were obtained 27.6 g of a fraction consisting of 95.5% by weight of 2-methyl-1-buten-4-ol and 4.5% by weight of water, 11.7 g of a fraction consisting of 96.1% by weight of 2-methyl-1-buten-4-al and 3.9% by weight of water, 7.9 g of a fraction containing 95.7% by weight of 2-methyl-2-buten-4-al and 2.6 g of a fraction consisting of 93.5% by weight of isovaleraldehyde and 6.5% by weight of water. Water remained in the still, but as a result of analysis, contained no detectable amounts of the above constituents

EXAMPLE 11

A 500 cc stainless steel autoclave equipped with a manometer, a safety valve and an electrolmagnetically stirring device was charged with commercially available paraformaldehyde (purity 97.7%) and isobutylene in the ratios shown in Table 11.

The temperature was elevated to 230° C. over the course of about 40 to 50 minutes, and then, the above starting materials were reacted for 1.5 hours. The autoclave was cooled, and the unreacted matter was purged. The product was withdrawn, and analyzed by gas-chromatography. The formation of 2-methyl-1-buten-4-ol was noted. The conversion based on the paraformaldehyde and the selectivity to the 2-methyl-1-buten-4-ol are shown in Table 11.

Table 11

| Runs | Ratio of isobutylene/Paraformaldehyde (mol/mol) | Reaction Conditions Temperature (° C) | Time (hours) | Results of the reaction Conversion of formaldehyde (%) | Selectivity to 2-methyl-1-buten-4-ol |
|---|---|---|---|---|---|
| 11-(1) | 0.96/1 | 230 | 1.5 | 98.7 | 25.6 |
| 11-(2) | 2.0/1 | 230 | 1.5 | 97.0 | 43.0 |
| 11-(3) | 3.0/1 | 230 | 1.5 | 96.8 | 56.0 |
| 11-(4) | 4.0/1 | 230 | 1.5 | 92.1 | 63.0 |
| 11-(5) | 9.6/1 | 230 | 1.5 | 95.6 | 83.7 |
| 11-(6) | 19/1 | 230 | 1.5 | 98.6 | 89.5 |

EXAMPLE 12

In quite the same way as in Example 11, paraformaldehyde and isobutylene were charged into the autoclave in the ratio shown in Table 12, and reacted under the reaction conditions shown in Table 12. The results are shown in Table 12. The conversion and the selectivity are based on formaldehyde.

Table 12

| Runs | Ratio of isobutylene/formaldehyde (mol/mol) | Reaction Conditions Temperature (° C) | Time (hours) | Results of reaction Conversion of formaldehyde (%) | Selectivity to 2-methyl-1-buten-4-ol |
|---|---|---|---|---|---|
| 12-(1) | 9.4/1 | 200 | 4 | 88.5 | 76.5 |
| 12-(2) | 9.4/1 | 270 | 1.5 | 96.7 | 78.5 |
| 12-(3) | 9.4/1 | 340 | 0.5 | 91.0 | 74 |
| 12-(4) | 9.4/1 | 400 | 0.25 | 92.1 | 62.3 |

EXAMPLE 13

Run No. 13-(1)

30 Parts of commercially available paraformaldehyde (purity 97% as $CH_2O$) was suspended in 450 parts of isobutylene to form a slurry. The slurry was continuously fed into a reaction pipe immersed in a heat transfer medium kept at 250° C. The reaction product withdrawn from the reaction pipe was immediately cooled to about 50° C. The residence time in the reactor was $$20\left(\frac{l\ \text{reactor}}{l/\text{minute slurry}}\right).$$

The reactor was clogged in about 7 hours after the initiation of feeding the slurry. The product was seen to contain particles having a diameter of about 0.1 mm to 2 mm and colored brown to black, and this led to the presumption that the reactor had been clogged. Based on the paraformaldehyde, the conversion was 97%, and the selectivity was 40%. The colored particles contained 6 to 7% of the paraformaldehyde.

Run No. 13-(2)

When the temperature of the reactor was changed to 200° C. in the procedure of Run No. 13-(1), the reactor was clogged in about 35 hours. Based on the paraformaldehyde, the conversion was 60%, and the selectivity was 45%.

Runs Nos. 13-(3) to 13-(10)

In the procedure of Run No. 13-(1), two reaction cylinders were connected in series to the back of the pipe of the reactor. The same procedure as in Run No. 13-(1) was repeated except that the temperature of the reaction pipe, the temperature of the reaction cylinders and the residence time were varied as shown in Table 13. The conversions and selectivities based on the paraformaldehyde are shown in Table 13.

Table 13

| Run No. | Ratio of isobutylene/formaldehyde (mol/mol) | Conditions Preheating Temperature (° C) | Time (min.) | Reaction Conditions Temperature (° C) | Time (min.) | Results of reaction Conversion of formaldehyde % | Selectivity of 2-methyl-1-buten-4-ol (%) | Remarks |
|---|---|---|---|---|---|---|---|---|
| 13-(1) | 8.2/1 | — | — | 250 | 20 | 97.0 | 40.0 | Control |
| 13-(2) | " | — | — | 200 | 20 60 | 45 | Control | |
| 13-(3) | " | 60 | 20 | 265 | 20 | 88.2 | 51.5 | Control (clogged) |
| 13-(4) | " | 100 | 20 | 265 | 20 | 82.2 | 82.5 | Invention |
| 13-(5) | " | 125 | 20 | 265 | 20 | 82.0 | 88.6 | " |
| 13-(6) | " | 125 | 20 | 230 | 60 | 93.5 | 90.5 | " |
| 13-(7) | " | 135 | 20 | 265 | 20 | 87.2 | 77.5 | " |
| 13-(8) | " | 150 | 20 | 265 | 20 | 80.4 | 69.3 | " |

Table 13-continued

| Run No. | Ratio of isobutylene/ formaldehyde (mol/mol) | Preheating Temperature (°C) | Preheating Time (min.) | Reaction Conditions Temperature (°C) | Reaction Conditions Time (min.) | Conversion of formaldehyde % | Selectivity of 2-methyl-1-buten-4-ol (%) | Remarks |
|---|---|---|---|---|---|---|---|---|
| 13-(9) | " | 160 | 20 | 265 | 20 | 77.7 | 89.3 | Control (clogged) |
| 13-(10) | " | 200 | 20 | 265 | 20 | 85.0 | 71.2 | Control (clogged) |

EXAMPLE 14

The procedure of Example 11-(1) was repeated except that a 37% aqueous solution of formaldehyde was used in the amount shown in Table 4 instead of the paraformaldehyde. The results are shown in Table 14.

Table 14

| Run No. | Ratio of isobutylene/ formaldehyde (mol/mol) | Ratio of Solvent/ formaldehyde (mol/mol) | Conversion of formaldehyde % | Selectivity to 2-methyl 1-buten-4-ol % | Remarks |
|---|---|---|---|---|---|
| 14-(1) | 1.0/1 | Water (2.84) | 96.2 | 15.9 | Control |
| 14-(2) | 5.0/1 | " | 95.3 | 28.5 | Control |
| 14-(3) | 10.0/1 | " | 94.4 | 51.7 | Control |

EXAMPLE 15

The procedure of Example 11-(1) was repeated except that benzene or cyclohexane was used in the proportions shown in Table 15 in addition to the paraformaldehyde and isobutylene. The results are shown in Table 15.

Table 15

| Run No. | Ratio of formaldehyde/isobutylene (mol/mol) | Ratio of solvent/ formaldehyde (mol/mol) | Conversion of formaldehyde % | Selectivity to 2-methyl-1-buten-4-ol % | Remarks |
|---|---|---|---|---|---|
| 15-(1) | 9.6/1 | Benzene (1.5) | 88.1 | 90.3 | Invention |
| 15-(2) | 9.6/1 | Cyclohexane (1.4) | 80.1 | 89.3 | Invention |

EXAMPLE 16

The procedure of Example 13-(5) was repeated except that 1.5 mols, per mol of the paraformaldehyde, benzene was added. Based on the formaldehyde, the conversion was 84.5%, and the selectivity to 2-methyl-1-buten-4-ol was 92.5%.

EXAMPLE 17

The procedure of Example 11-(1) was repeated except that propylene or butene-1was used instead of the isobutylene in the proportion shown in Table 16. There were obtained 1-buten-4-ol and 2-penten-5-ol, respectively. The results are shown in Table 16.

Table 16

| Run No. | Ratio of olefin/ formaldehyde (mol/mol) | Conversion of formaldehyde (%) | Selectivity of alcohol (%) | Remarks |
|---|---|---|---|---|
| 17-(1) | Propylene (5/1) | 41 | 97* | Invention |
| 17-(2) | Butene-1 (5/1) | 83 | 28** | Invention |

*1-buten-4-ol
**2-penten-5-ol

EXAMPLE 18

20 g of a raw material consisting of 26.80% by weight of 2-methyl-1-buten-4-al, 31.82% by weight of isovaleraldehyde, 16.22% by weight of 2-methyl-2-buten-4-al and 17.37% of 2-methyl-1-buten-4-ol and 5 g of water were charged into a still of a spinning band-type distillation tower (6 mm$\phi$ × 1800 mml), and distilled at a reflux ratio of 50 and a pressure of 200 mmHg abs. The fractions obtained were analyzed by gas-chromatography, and the results are shown in Table 17. In this distillation process, water was continuously fed into the still at a rate of 10 cc/hour, and the distillate was separated into an organic liquid phase and an aqueous phase. The oily phase was analyzed, and the results are shown in Table 17.

Table 17

| Distillate No. | Temperature of the top of column (°C) | 2-Methyl-1-buten-4-al | Isovaleraldehyde | 2-Methyl-2-buten-4-al | 2-Methyl-1-buten-4-ol |
|---|---|---|---|---|---|
| 1 | 38 | 21.60 | 77.60 | 0 | 0 |
| 2 | 38 | 65.20 | 33.30 | 0 | 0 |
| 3 | 39 | 88.80 | 8.40 | 0 | 0 |
| 4 | 38 | 93.50 | 3.00 | 0 | 0 |
| 5 | 38 | 42.90 | 2.70 | 35.5 | 1.3 |
| 6 | 38 | 5.10 | 1.40 | 50.3 | 0.18 |
| 7 | 57 | 1.70 | 1.30 | 88.5 | 0.40 |
| 8 | 58 | 2.50 | 1.20 | 44.4 | 49.6 |
| 9 | 58 | 1.00 | 0.81 | 2.0 | 94.4 |
| 10 | 58 | 1.10 | 0.86 | 0.6 | 96.9 |
| 11 | 60 | 2.60 | 0 | 0 | 97.3 |
| Residue | — | 0 | 0 | 0 | 0 |

The aqueous phase resulting after the separation of the organic phase was analyzed, and found to contain 0.98% of weight of 2-methyl-1-buten-4-al, 0.09% by weight of isovaleraldehyde, 4.93% by weight of 2-methyl-2-buten-4-al, and 0.09% of 2-methyl-1-buten-4-ol.

Referential Example 4

20 g of a raw material consisting of 28.99% by weight of 2-methyl-1-buten-4-al, 49.12% by weight of isovaleraldehyde, 2.83% by weight of 2-methyl-2-buten-4-ol and 4.19% by weight of 2-methyl-1-buten-4-ol was charged into the same distillation tower as in Example 18, and distilled at a reflux ratio of 50 and a pressure of 200 mmHg (absolute). The distillate was analyzed, and the results are shown in Table 18.

Table 18

| Distillate No. | Temperature of the tower (° C) | Analysis of the distillate (%) | | | |
|---|---|---|---|---|---|
| | | 2-Methyl-1-buten-4-al | Isovaleraldehyde | 2-Methyl-2-buten-4-al | 2-Methyl-1-buten-4-ol |
| 1 | 40 | 46.21 | 51.43 | 0 | 0.53 |
| 2 | 40 | 68.83 | 46.77 | 0 | 0 |
| 3 | 42 | 57.66 | 41.32 | 0 | 4.06 |
| 4 | 45 | 43.15 | 19.80 | 24.59 | 5.24 |
| 5 | 60 | 47.21 | 13.01 | 8.50 | 4.90 |
| 6 | 60 | 0.02 | 8.25 | 0.11 | 80.80 |
| Residue | — | 0 | 0 | 11.04 | 86.50 |

What we claim is:

1. A process for preparing α,γ-unsaturated aldehydes of the formula

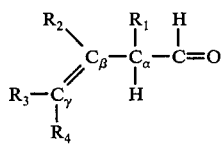

wherein $R_1$, $R_2$ and $R_3$ are identical or different and represent a hydrogen atom or a methyl group, and $R_4$ is a hydrogen atom or a linear or cyclic saturated or unsaturated hydrocarbon residue containing 1 to 6 carbon atoms, which comprises contacting a β,γ-unsaturated alcohol of the formula

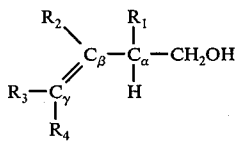

wherein $R_1$, $R_2$, $R_3$ and $R_4$ are the same as defined above, in the vapor phase with metallic copper prepared by reduction of copper oxide having a specific surface area of 0.10 to 0.92 m²/g as a catalyst at a temperature of 200° to 280° C in the presence of a carrier gas and in the substantial absence of oxygen.

2. The process of claim 1 wherein said contacting is carried out while maintaining the weight of said β,δ-unsaturated alcohol per unit weight of said catalyst per hour (WHSV) at 0.01 to 1.0 g/g.hr.

3. The process of claim 1 wherein said contacting is carried out in the presence of steam.

4. The process of claim 3 wherein the amount of steam is 2 to 50 mols per mol of the β, δ-unsaturated alcohol.

5. The process for preparing β-,γ-unsaturated aldehydes according to claim 1 wherein said β-,γ-unsaturated alcohol is selected from the group consisting of 1-buten-4-ol, 2-methyl-1-buten-4-ol, 2,3-dimethyl-1-buten-4-ol, 3-methyl-1-buten-4-ol, 2-penten-5-ol, 2-methyl-2-penten-5-ol, 3-methyl-2-penten-5-ol, 3-hexen-6-ol, 3-methyl-3-hexen-6-ol, 4-methyl-3-hexen-6-ol, 4-methyl-1,3-hexadien-6-ol, 5-methyl-4-hepten-7-ol, 2,4-dimethyl-3-hexen-7-ol, 6-methyl-5-octene-8-ol, 2,5-dimethyl-4-hepten-7-ol, 2,5-dimethyl-2,4-heptadien-7-ol, 2,6-dimethyl-2,4-heptadien-7-ol, 2,6-dimethyl-5-octen-8-ol, 2,6-dimethyl-2,5-octadien-8-ol, 1-cyclohexyl-1-buten-4-ol, 1-cyclohexyl-2-methyl-1-buten-4-ol, 1-phenyl-1-buten-4-ol, and 1-phenyl-2-methyl-1-buten-4-ol.

6. The process for preparing β-,γ-unsaturated aldehydes according to claim 1 wherein said β-, γ-unsaturated alcohol is 2-methyl-1-buten-4-ol.

7. The process for preparing β,δ-unsaturated aldehydes according to claim 1 wherein the partial pressure of the β-, γ-unsaturated alcohol is from 0.01 to 0.2 atmospheres.

8. The process for preparing β, γ-unsaturated aldehydes according to claim 4 wherein the partial pressure of the β-,γ-unsaturated alcohol is from 0.01 to 0.2 atmospheres.

9. A process for preparing β,γ-unsaturated aldehydes of the formula

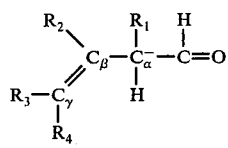

wherein $R_1$, $R_2$ and $R_3$ are identical or different and represent a hydrogen atom or a methyl group, and $R_4$ is a hydrogen atom or a linear or cyclic saturated or unsaturated hydrocarbon residue containing 1 to 6 carbon atoms, which comprises (1) reacting an olefin of the formula

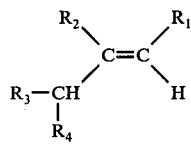

wherein $R_1$, $R_2$, $R_3$ and $R_4$ are the same as defined above, with formaldehyde or a derivative capable of forming formaldehyde at the reaction temperature, at a reaction temperature of 200° to 340° C. in the absence of a solvent or in the presence of a non-aqueous organic solvent selected from the group consisting of halogenated hydrocarbons, diethyl ether, tetrahydrofuran, paradioxane, tetrahydropyran, aliphatic hydrocarbons, alicyclic hydrocarbons, aromatic hydrocarbons and dioxanes after pre-heating said formaldehyde or derivative to a temperature of 85° to 150° C. thereby to form a β, γ-unsaturated alcohol of the formula

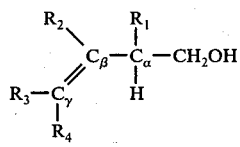

wherein $R_1$, $R_2$, $R_3$ and $R_4$ are the same as defined above, and (2) contacting the β,γ-unsaturated alcohol in the vapor phase with metallic copper prepared by reduction of copper oxide having a specific surface area of 0.10 to 0.92 m²/g as a catalyst at a temperature of 200° to 280° C. in the presence of a carrier gas and in the substantial absence of oxygen.

10. The process according to claim 9 wherein step (1) is carried out with said derivative wherein said derivative is paraformaldehyde.

11. The process according to claim 9 wherein in step (1) the preheating is carried out at a temperature of 100° to 140° C.

12. The process according to claim 9 wherein in step (1) the amount of said olefin is at least 2n mols, wherein n is the number of double bonds contained in said olefin, per mol of the formaldehyde.

13. The process according to claim 9 wherein in step (1), said olefin is isobutylene.

14. The process according to claim 9 wherein step (1) is carried out in the presence of said non-aqueous organic solvent.

15. The process according to claim 14 wherein said non-aqueous organic solvent is selected from the group consisting of chloroform, 1,2-dichloroethane, diethylether, tetrahydrofuran, para-dioxane, tetrahydropyran, acetic acid, ethyl acetate, hexane, octane, n-heptane, cyclohexane, benzene, toluene, xylene and p-dioxane.

16. The process according to claim 9 wherein in step (2) said contacting is carried out while maintaining the weight of said $\beta,\gamma$-unsaturated alcohol per unit weight of said catalyst per hour (WHSV) at 0.01 to 1.0 g/g.hr.

17. The process according to claim 9 wherein in step (2) said contacting is carried out in the presence of steam.

18. The process according to claim 17 wherein the amount of steam is 2 to 50 mols per mol of the $\beta,\gamma$-unsaturated alcohol.

19. The process of claim 9 wherein in step (2) the partial pressure of the $\beta,\gamma$-unsaturated alcohol is from 0.01 to 0.2 atmospheres.

* * * * *

UNITED STATES PATENT AND TRADEMARK OFFICE
CERTIFICATE OF CORRECTION

PATENT NO. : 4,110,403
DATED : August 29, 1978
INVENTOR(S) : YATARO ICHIKAWA, ET AL.

It is certified that error appears in the above-identified patent and that said Letters Patent are hereby corrected as shown below:

Claim 1, line 19, delete "$\alpha$" and insert -- $\beta$ --

Claim 2, line 48, delete "$\delta$-" and insert --$\gamma$- --

Claim 4, line 54, delete "$\delta$-unsaturated" and insert -- $\gamma$-unsaturated --

Claim 7, line 6, delete "$\delta$-unsaturated and insert -- $\gamma$-unsaturated --

[SEAL]

Signed and Sealed this

Thirteenth Day of March 1979

Attest:

RUTH C. MASON
Attesting Officer

DONALD W. BANNER
Commissioner of Patents and Trademarks